(12) United States Patent
Salguero et al.

(10) Patent No.: US 7,993,797 B2
(45) Date of Patent: Aug. 9, 2011

(54) CHEMICALLY MODIFIED CATALYZED SUPPORT PARTICLES FOR ELECTROCHEMICAL CELLS

(75) Inventors: Tina T. Salguero, Encino, CA (US); Elena Sherman, Culver City, CA (US); Ping Liu, Irvine, CA (US)

(73) Assignee: GM Global Technology Operations LLC, Detroit, MI (US)

(*) Notice: Subject to any disclaimer, the term of this patent is extended or adjusted under 35 U.S.C. 154(b) by 1030 days.

(21) Appl. No.: 11/775,298

(22) Filed: Jul. 10, 2007

(65) Prior Publication Data

US 2010/0028745 A1    Feb. 4, 2010

(51) Int. Cl.
*H01M 4/36* (2006.01)
*C07C 309/00* (2006.01)

(52) U.S. Cl. ........ 429/523; 429/529; 429/530; 429/532; 562/42

(58) Field of Classification Search ............ 429/479, 429/492, 493, 494, 523, 529, 530, 532; 562/42; 564/418; 502/172, 168, 167, 162, 174, 180, 502/181
See application file for complete search history.

(56) References Cited

U.S. PATENT DOCUMENTS

| | | | |
|---|---|---|---|
| 5,554,739 A | | 9/1996 | Belmont |
| 5,900,029 A | | 5/1999 | Belmont et al. |
| 6,187,467 B1 | * | 2/2001 | Zhang et al. ............ 429/479 |
| 2005/0221141 A1 | * | 10/2005 | Hampden-Smith et al. .... 429/33 |

FOREIGN PATENT DOCUMENTS

| WO | WO 96/18688 | * | 6/1996 |
|---|---|---|---|
| WO | WO 2005/091416 A2 | | 9/2005 |

OTHER PUBLICATIONS

N. Tsubokawa. Functionalization of Carbon Black by Surface Grafting of Polymers, Prog. Polym. Sci. 1992, 17, 417-470.*
C. Heitner-Wirguin. Recent advances in perfluorinated ionomer membranes: structure, properties and applications, J. Membr. Sci. 1996, 120, 1-33).*
HK. Kim, W. Lee, D. Yoo. Functionalized carbon support with sulfonated polymer for direct methanol fuel cells, Electrochimica Acta 2007, 52, 2620-2624.*
H. Mizuhata, S.-i. Nakao, T. Yamaguchi. Morphological control of PEMFC electrode by graft polymerization of polymer electrolyte onto platinum-supported carbon black, J. Power Sources 2004, 138, 25-30.*
Z. Poltarzewski, P. Staiti, V. Alderucci, W. Wieczorek, and N. Giordano. Nafion Distribution in Gas Diffusion Electrodes for Solid-Polymer-Electrolyte-Fuel-Cell Applications, J. Electrochem. Soc. 1992, 139, 761-765.*
Zhiqiang Xu, Zhigang Qi, and Arthur Kaufman, "Hydrophobization of Carbon-Supported Catalysts..." Electrochemical and Solid-State Letter, 8 (10) A492-A494 (2005), New York, US.

* cited by examiner

*Primary Examiner* — Jennifer K. Michener
*Assistant Examiner* — Carlos Barcena
(74) *Attorney, Agent, or Firm* — Reising Ethington P.C.

(57) ABSTRACT

A membrane-electrode assembly in a polymer electrolyte/proton exchange membrane fuel cell includes the electrodes (anode and cathode), with a thin layer of catalyzed conductive support particles bonded to either side of the membrane. Where the polymer membrane comprises pendant chains of fluorinated carbon atoms with mobile proton containing terminal groups, proton conductivity with the catalyst particles is improved by chemically attaching like pendant chains to carbon atoms at surfaces of carbon particles. In certain implementations, an amino aryl perfluorinated sulfonic acid precursor is prepared. This precursor is converted to an aryl diazonium cation in the presence of carbon particles. The diazonium cation is reduced to the aryl radical which reacts with carbon atoms of the carbon substrate.

7 Claims, 4 Drawing Sheets

CHEMICALLY MODIFIED CATALYZED SUPPORT PARTICLES FOR ELECTROCHEMICAL CELLS

TECHNICAL FIELD

This disclosure pertains to the treatment of catalyst support materials for use with fuel cells.

BACKGROUND OF THE INVENTION

Fuel cells are electrochemical cells that are being developed for mobile and stationary electric power generation. One fuel cell design uses a solid polymer electrolyte (SPE) membrane or proton exchange membrane (PEM), to provide ion transport between the anode and cathode. Gaseous and liquid fuels capable of providing protons are used. Examples include hydrogen and methanol, with hydrogen being favored. Hydrogen is supplied to the fuel cell anode. Oxygen (as air) is the cell oxidant and is supplied to the cell's cathode.

The membrane-electrode assembly (MEA) in a polymer electrolyte/proton exchange membrane fuel cell comprises the electrodes (anode and cathode), with a thin layer of catalyst, bonded to either side of the membrane. In principle, these materials act together to conduct electrons (from the anode to an external resistive circuit) from $H_2$ oxidation, transport $H^+$ (through the membrane), and conduct electrons to the cathode to the oxygen reduction catalyst to recombine $H^+$ with $O_2$. In practice, however, these materials are not optimally tuned for peak performance.

Nafion® is a widely used proton-conducting material because it possesses high proton conductivity, good mechanical strength, and good chemical and electrochemical stability under fuel cell operating conditions. These properties arise from the chemical compositions of Nafion® membranes which are a family of perfluorosulfonic acid ionomer membranes. Related ionomer materials include Flemion® and Aciplex® (produced by Asahi Glass and Asahi Kasei, respectively) and a Dow® ionomer. The backbones of the polymers comprise tetrafluoroethylene monomer units and trifluoroethylene monomer units that provide excellent oxidative stability to the membrane. Side chains of two or more —$OCF_2CF_2$— moieties (or analogs of these moieties) are attached to the backbone and each of these side chains is terminated by a sulfonic acid ion ($SO_3^-$). The total number and proportion of tetrafluoroethylene moieties and trifluoroethylene moieties per polymer molecule provides the membrane with its properties including a suitable abundance of pendant ionizable groups (e.g. sulfonate groups) for transport of protons through the membrane from the anode to the cathode when the membrane is suitably hydrated. The large electronegativity of the fluorine atoms bonded to the same carbon atom as the sulfonic acid group makes this group strongly acidic. In the example of Nafion 117 membrane, the equivalent weight (g ionomer/mol $SO_3^{-1}$) is about 1100.

The fuel cell electrodes are generally composed of a mixture of high surface area carbon-supports (0.1 to 1 micrometer particles or particle agglomerates) on which nanometer sized electrochemically active catalyst particles are supported (typically 2 to 20 nanometer sized platinum, platinum-group metals, or alloys thereof, as well as alloys of platinum or platinum-group metals with transition metals) and binder. Binders are typically perfluorinated polymers (e.g., PTFE, FEP, etc.) or sulfonic acid based polymers (e.g., perfluorosulfonic acid ionomers). These electrodes are sandwiched between the ionic membrane and porous conductive materials, such as woven graphite, graphitized sheets, or carbon paper (commonly referred to as diffusion media or gas diffusion layers). Depending on whether electrodes are supported on the ionomeric membrane or on the gas diffusion layer, the assemblies are referred to as catalyst-coated membranes or catalyst-coated diffusion media (also called gas diffusion electrodes), respectively. The electrochemical fuel cell reactions—the anodic oxidation of hydrogen or other fuels and the cathodic reduction of oxygen (from air)—occur throughout the electrodes on the active catalyst particles. For the electrochemical reactions to occur, protons need to be conducted throughout the electrodes into and out of the ionomeric proton-conducting membrane. This invention is based on a need to improve the proton conduction ability of fuel cell electrodes that may or may not contain proton conducting ionomeric binder, thereby improving fuel cell performance and durability.

SUMMARY OF THE INVENTION

In one embodiment of this invention, carbon catalyst support particles for inclusion in a fuel cell electrode layer are chemically modified to provide the carbon surfaces with chemical characteristics of the ionomer with which the particles are associated. The carbon particles are electrically conductive and commonly consist of 20 to 100 nanometer primary carbon particles that form primary agglomerates of 0.1 to five micrometers. The electrochemically active catalyst supported on the carbon support particles are typically two to twenty nanometer sized platinum, platinum-group metals or alloys thereof, as well as alloys of platinum or platinum-group metals with transition metals. Chemical groups similar to proton conducting pendant groups of the ionomer and fuel cell membrane molecules are prepared and chemically attached to carbon atoms at surfaces of the carbon particles. In general the chemical groups are attached to the carbon particles after the electrochemically active catalyst nanoparticles are deposited on the carbon support material and before the catalyzed carbon particles are incorporated into an electrode.

In an embodiment when a Nafion® membrane (or a like perfluorosulfonic acid ionomer membrane) material is used, groups comprising —$OCF_2CF_2$— moieties (or the like) and terminal sulfonic acid groups (or other group containing a mobile proton) are prepared and chemically attached to the carbon particles. Thus, the chemical groups attached to surfaces of the carbon support particles may include an unreactive fluorinated portion and a highly acidic sulfonic acid group.

In a preferred Nafion® or Nafion®-like ionomer membrane embodiment, the added chemical group is a linear fluorinated carbon molecular chain structure that includes an oxygen atom:

particle-Ar—$(CF_2)_a$—O—$(CF_2)_b$—X, where

Ar=any aromatic or conjugated moiety, but preferably an aryl ring
a=0 to 500, but preferably an even number between 2 and 50
b=0 to 500, but preferably an even number between 2 and 50, provided that at least one of a and b is not equal to 0
X=any moiety with a mobile proton, including but not limited to $SO_3H$, $CO_2H$, $P(O)(OH)_2$, $P(O)(OH)(CF_3)$, $SO_2NHSO_2CF_3$, with the preferred embodiment being $SO_3H$.

In other embodiments the added chemical group may include linear branching structures of fluorinated carbons that include an oxygen atom, such as:

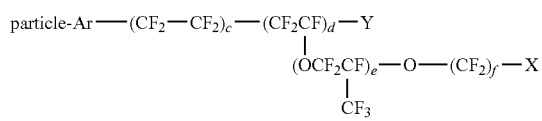

Ar=as above
Y=a terminal group including but not limited to $CF_3$, $CF_2$, OH
c=0 to 20
d=0 to 1000
e=0 to 10
f=0 to 10, provided that at least one of c, d, e, and f is not equal to 0
X=as above In many embodiments of the invention the carbon particles may be an electrical conductive carbon black material such as Vulcan® carbon black particles, Ketjen® black carbon, Black Pearls® carbon black, acetylene black carbon, etc.

A sequence of chemical reactions are provided for preparing fluorinated carbon molecular chains that include at least one oxygen atom and have terminal sulfonic acid precursor groups (or other mobile proton containing groups), and for attaching such molecular chains to suitable carbon particles. In one embodiment of the invention, an amino aryl perfluorinated sulfonyl fluoride is prepared. This precursor is converted to an aryl diazonium cation in the presence of carbon particles. The diazonium cation is reduced to the aryl radical which reacts with carbon atoms at surfaces of the carbon substrate particles. Thus, proton conductive sulfonic acid terminated chains are appended to carbon support surfaces on which the electrochemically active catalyst nanoparticles (e.g., platinum nanoparticles) are supported.

In another embodiment of the invention the carbon particles carrying proton conductive groups are incorporated into an electrode material and applied as an electrode layer onto a surface of a proton conductive fuel cell membrane. This electrode material may be used in formulating either the cathode or anode of the fuel cell, or both electrodes.

A fuel cell often comprises a stack of many individual cells each comprising a membrane with its electrodes each comprising catalyst support particles of carbon. In another embodiment of the invention carbon particles with attached oxygen-containing fluorocarbon chains and proton conductive groups may be used in several or all of the electrode compositions in the stacked cells.

In other embodiments of the invention, molecular species prepared as aryl diazonium cations may be reacted with carbon particles in other applications in which it is desired to adapt the surfaces of the particles to an adjacent or surrounding material environment. Further, molecular species with attached fluorocarbon chains and mobile-proton containing groups prepared as aryl diazonium cations may be reacted with other carbon sources, including but not limited to graphite, carbon nanotubes, and C60, or even reacted with non-carbon surfaces, including but not limited to metals or oxides.

Other embodiments and advantages of the invention will be apparent from descriptions of certain preferred embodiments that follow.

DESCRIPTION OF PREFERRED EMBODIMENTS

Many United States patents assigned to the assignee of this invention describe electrochemical fuel cell assemblies having an assembly of a solid polymer electrolyte membrane and electrode assembly. For example, FIGS. 1-4 of U.S. Pat. No. 6,277,513 include such a description, and the specification and drawings of that patent are incorporated into this specification by reference.

Figure 1:
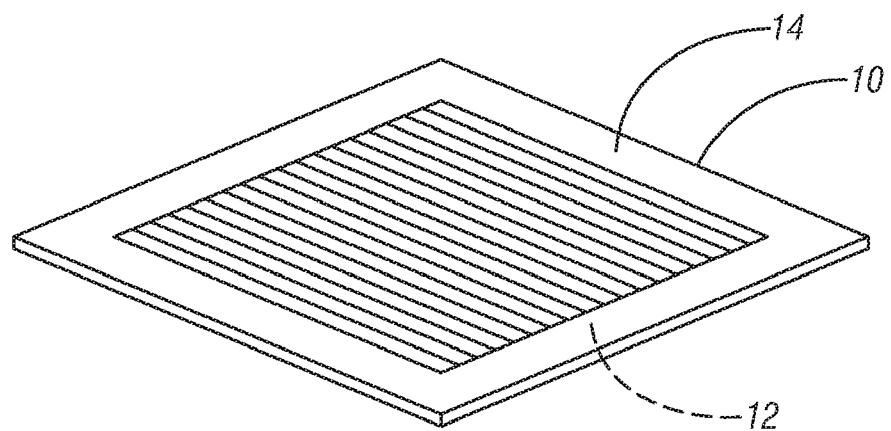
FIG. 1 is a schematic view of a combination of solid polymer membrane electrolyte and electrode assembly (MEA) used in each cell of an assembled fuel cell stack.

FIG. 1 of this application illustrates a membrane electrode assembly 10 which is a part of the electrochemical cell illustrated in FIG. 1 of the '513 patent. Referring to FIG. 1 of this specification, membrane electrode assembly 10 includes anode 12 and cathode 14. In a hydrogen/oxygen (air) fuel cell, for example, hydrogen is oxidized to $H^+$ (proton) at the anode 12 and oxygen is reduced to water at the cathode 14.

Figure 2:
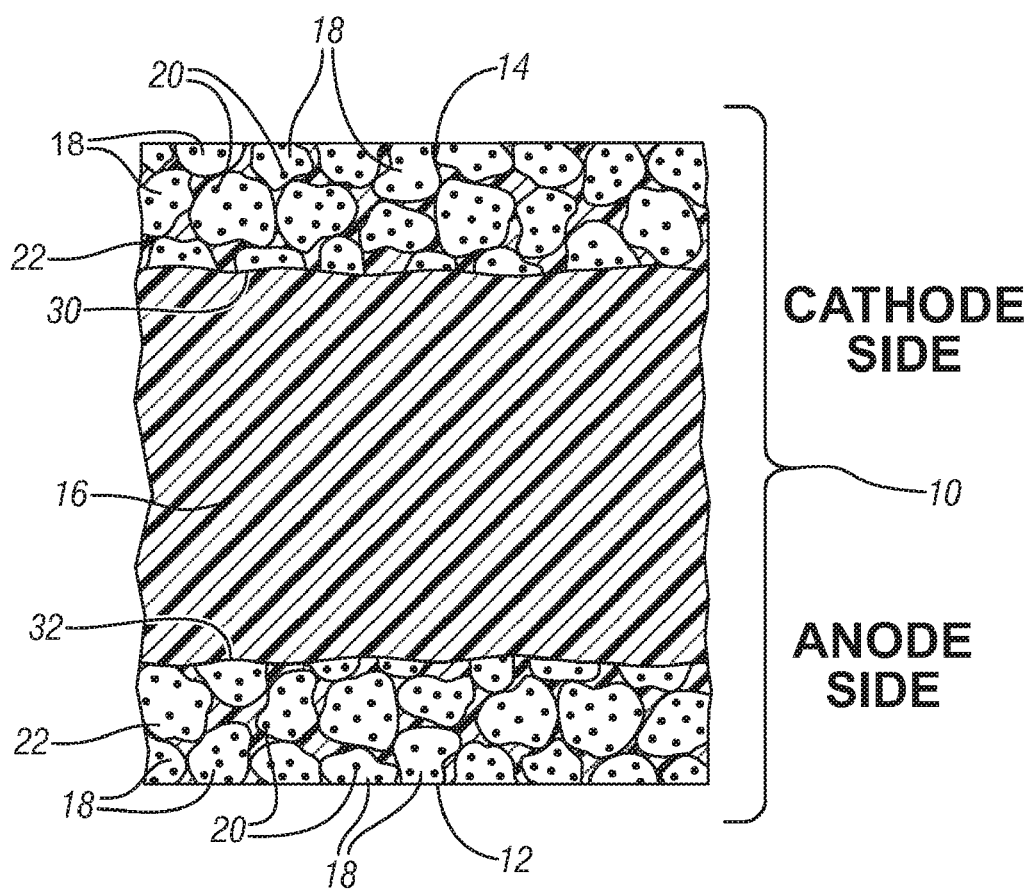
FIG. 2 is an enlarged fragmentary cross-section of the MEA of FIG. 1.

FIG. 2 provides a greatly enlarged, fragmented, cross-sectional view of the membrane electrode assembly shown in FIG. 1. In FIG. 2, anode 12 and cathode 14 are applied to opposite sides (sides 32, 30 respectively) of a proton exchange membrane 16. PEM 16 is suitably a membrane made of a perfluorinated ionomer such as DuPont's Nafion® 117 membranes. The ionomer molecules of the membrane carry pendant ionizable groups (e.g. sulfonic acid groups) for transport of protons through the membrane from the anode 12 applied to the bottom surface 32 of the membrane 16 to the cathode 14 which is applied to the top surface 30 of the membrane 16. In an exemplary cell, the polymer electrolyte membrane 16 may have dimensions of 100 mm by 100 mm by 0.05 mm. As will be described, the anode 12 and cathode 14 are both thin, porous electrode members prepared from catalyst inks (comprising catalyzed carbon-supports, binder, and suitable solvents) and applied directly to the opposite surfaces 30, 32 of the PEM 16.

Figure 7:
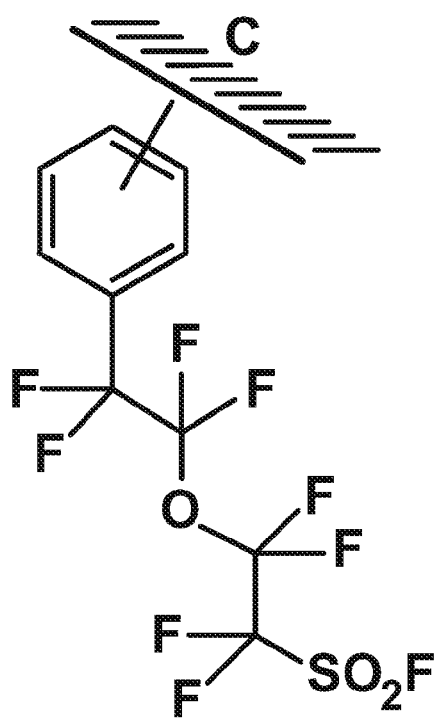
FIG. 7 is a schematic illustration of a chain of —$C_6H_4$—$(CF_2)_2$—O—$(CF_2)_2$—$SO_2F$ attached to a carbon particle.
Figure 8:
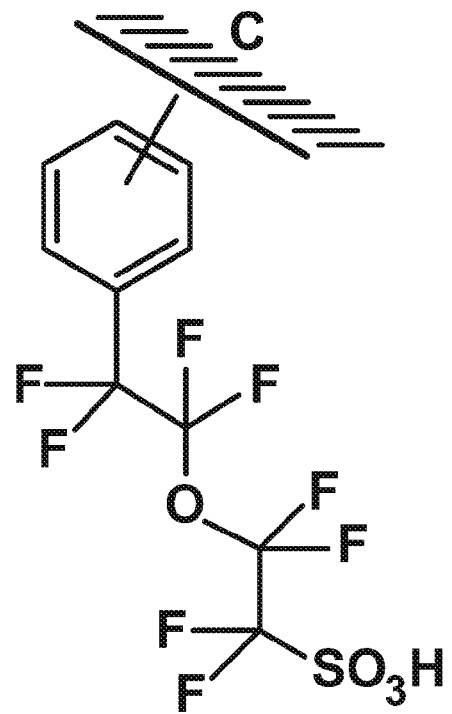
FIG. 8 is a schematic illustration of a chain of —$C_6H_4$—$(CF_2)_2$—O—$(CF_2)_2$—$SO_3H$ attached to a carbon particle.

In one embodiment cathode 14 suitably comprises submicrometer size, electrically conductive carbon black catalyst support particles 18 such as particles of Vulcan XC-72. The carbon catalyst support particles 18 carry smaller (e.g., nanometer size) particles 20 of a reduction catalyst for oxygen, such as platinum or of an oxidation catalyst for hydrogen. The platinum bearing carbon support particles 18 are also chemically modified in accordance with an embodiment of this invention. The chemical groups reacted with and attached to surfaces of carbon particles 18 are not shown in FIG. 2 but are illustrated schematically in FIGS. 7 and 8 as will be described further in this specification.

The platinized carbon support particles 18 are embedded in a suitable bonding material 22. Preferably a sufficient number of the electrically conductive support particles 18 are touching each other to provide electrical conductivity through bonding material 22. In this embodiment, the bonding material 22 is suitably a perfluorinated ionomer material like the polymer electrolyte membrane 16 material. The perfluorinated ionomer bonding material 22 conducts protons, but typically is not a conductor of electrons.

Figure 3:
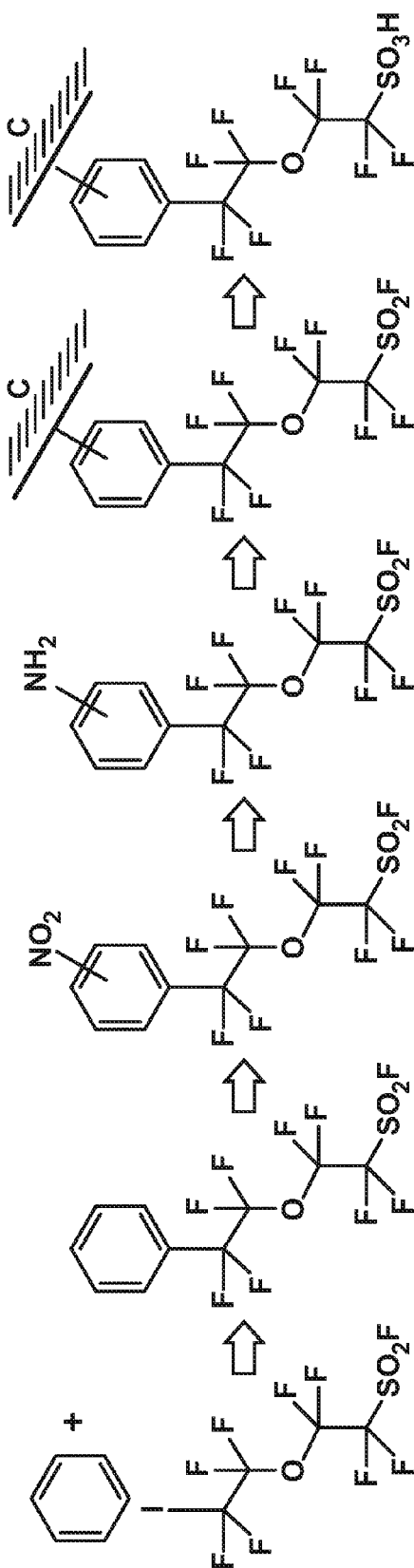
FIG. 3 illustrates a sequence of chemical reactions by which fluorosulfonic acid chains are prepared as aryl diazonium cations and chemically attached to surfaces of carbon particles.
Figure 4:
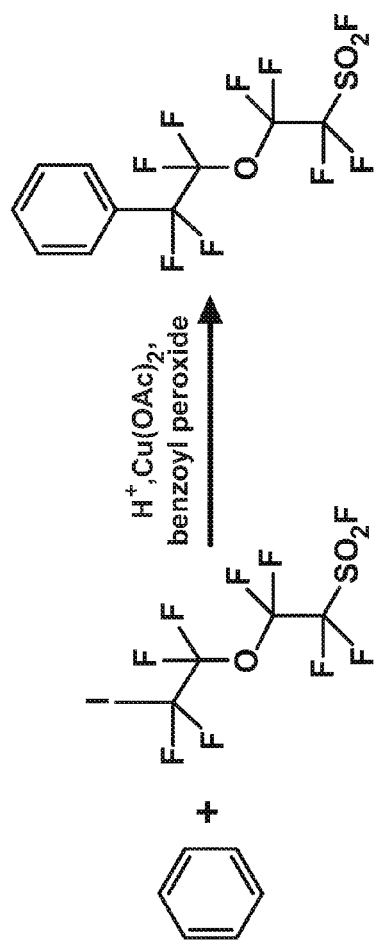
FIG. 4 illustrates a chemical reaction for the formation of $C_6H_5$—$(CF_2)_2$—O—$(CF_2)_2$—$SO_2F$.

As stated, the carbon support particles are chemically modified to carry pendant fluorosulfonic acid groups. FIG. 3 illustrates an illustrative sequence of five reaction steps in an embodiment of the invention by which side chains like those incorporated in Nafion® membranes may be chemically added to conductive carbon particles such as Vulcan XC-72 carbon black particles. This embodiment results in catalyst support particles of the formula:

Particle-Ar—$(CF_2)_a$—O—$(CF_2)_b$—X, where particle=carbon or Pt/carbon, Ar=$C_6H_4$, a=2, b=2, and X=$SO_3H$.

In the first reaction step illustrated in FIG. 3, $C_6H_5$—$(CF_2)_2$—O—$(CF_2)_2$—$SO_2F$ is prepared by coupling I—$(CF_2)_2$—O—$(CF_2)_2$—$SO_2F$ to benzene through a free-radical perfluoroalkylation method. In other embodiments other conjugated or aromatic ring systems, including but not limited to toluene or a xylene may be used in place of benzene.

In the second reaction step illustrated in FIG. 3, the phenyl group of $C_6H_5$—$(CF_2)_2$—O—$(CF_2)_2$—$SO_2F$ is nitrated under conditions developed for strongly electronically deactivated aromatic substrates. A reagent for this transformation, $NO_2^+BF_4^-$ in $CF_3SO_3H$, significantly enhances the nitrating ability of the nitronium species.

In the third step, the nitro group of $O_2N$—$C_6H_4$—$(CF_2)_2$—O—$(CF_2)_2$—$SO_2F$ is reduced to the amine under standard conditions using $SnCl_2$ in aqueous HCl. $H_2N$—$C_6H_4$—$(CF_2)_2$—O—$(CF_2)_2$—$SO_2F$ is now a reagent that can be used to functionalize the surface of carbon and effectively heterogenize the desired functional groups.

In the fourth step, $H_2N$—$C_6H_4$—$(CF_2)_2$—O—$(CF_2)_2$—$SO_2F$ is converted to an aryl diazonium cation. Diazonium species may be generated and optionally isolated using standard chemistries. The reduction of an aryl diazonium cation produces an aryl radical (Ar), which can attack various surfaces to form an X—Ar bond (where X=C, Fe, Cu, Si, Pt, and so on). This reduction reaction may be induced using electrochemically reducing conditions, chemical conditions, or it may occur spontaneously on clean surfaces. When the reduction occurs in the presence of a carbon surface, such as Vulcan carbon black, the generated aryl radical reacts with carbon atoms of the carbon substrate. The aryl radicals typically first attach at cleavage steps in the carbon and later on basal plane sites, which likely occurs at atomic-scale defects. This sequence covalently bonds the $C_6H_4$—$(CF_2)_2$—O—$(CF_2)_2$—$SO_2F$ group to the Vulcan, providing carbon-$C_6H_4$—$(CF_2)_2$—O—$(CF_2)_2$—$SO_2F$.

In the fifth step, the sulfonyl fluoride group of carbon-$C_6H_4$—$(CF_2)_2$—O—$(CF_2)_2$—$SO_2$ is converted to sulfonic acid by hydrolysis under strong conditions.

Experimental details of the five illustrative reactions are as follows.

Step 1: Preparation of $C_6H_5$—$(CF_2)_2$—O—$(CF_2)_2$—$SO_2F$ (see also FIG. 4)

7.82 g (100 mmol) of benzene, 8.52 g (20 mmol) of 5-iodooctafluoro-3-oxapentanesulfonyl fluoride, 4.84 g (20 mmol) of benzoyl peroxide, 0.36 g (2 mmol) of copper (II) acetate, and 100 mL of acetic acid were refluxed for 4 hrs at 115° C. Then the mixture was stirred at room temperature overnight. The mixture was diluted with water (~100 mL), and the product was extracted with hexane and washed with water until neutral pH was obtained. The solvent was removed to yield dark yellow oil. The product was purified by distillation under reduced pressure (~27 inch Hg). The first faction was composed of a mixture of the product plus iodobenzene (2.8 g, approximately 1:1 ratio). The second fraction consisted of 2.1 g of pure product (colorless oil) (28% yield).

Figure 5:
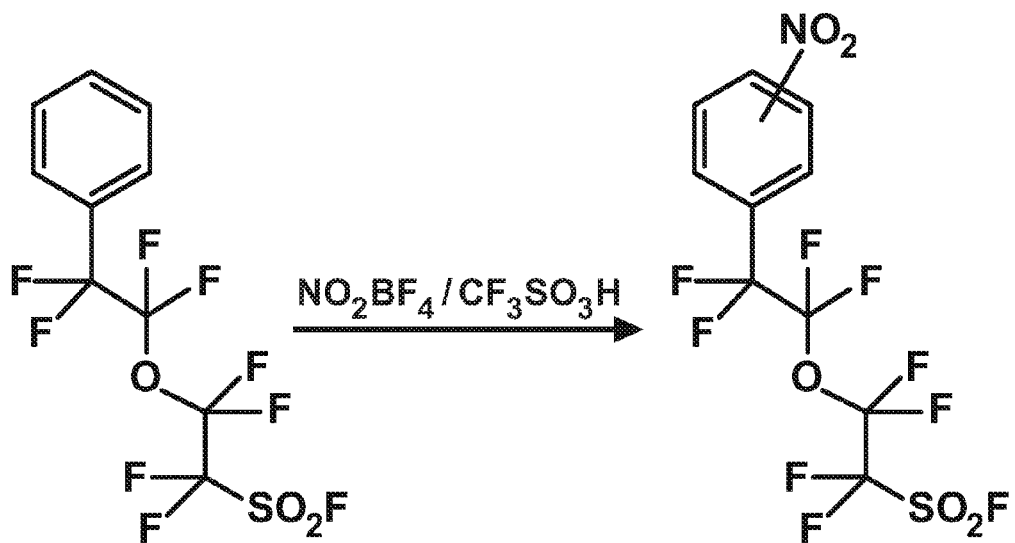
FIG. 5 illustrates a chemical reaction for the formation of $O_2N$—$C_6H_4$—$(CF_2)_2$—O—$(CF_2)$—$SO_2F$.

Step 2: Preparation of $O_2N$—$C_6H_4$—$(CF_2)_2$—O—$(CF_2)_2$—$SO_2F$ (see also FIG. 5)

10.0 mL (excess) of trifluoromethane sulfonic acid were placed in a round bottom flask and cooled to 0° C. 1.15 g (3.06 mmol) of $C_6H_4$—$(CF_2)_2$—O—$(CF_2)_2$—$SO_2F$ were added to the cold acid, followed by the addition of 0.407 g (3.06 mmol) of nitronium tetrafluoroborate. After stirring for 0.5 hr at 0° C. and another 3 hrs at room temperature, the reaction mixture was quenched with crushed ice. The product was extracted with dichloromethane. The organic layer was washed with water, aqueous $NaHCO_3$, and brine. The isolated organic layer was dried over $MgSO_4$. Evaporation of the solvent provided 1.036 g of dark brown oil (~80% yield). GC-MS analysis showed that this oil was composed of 92.2% product. This material was used without further purification for the next step.

Figure 6:
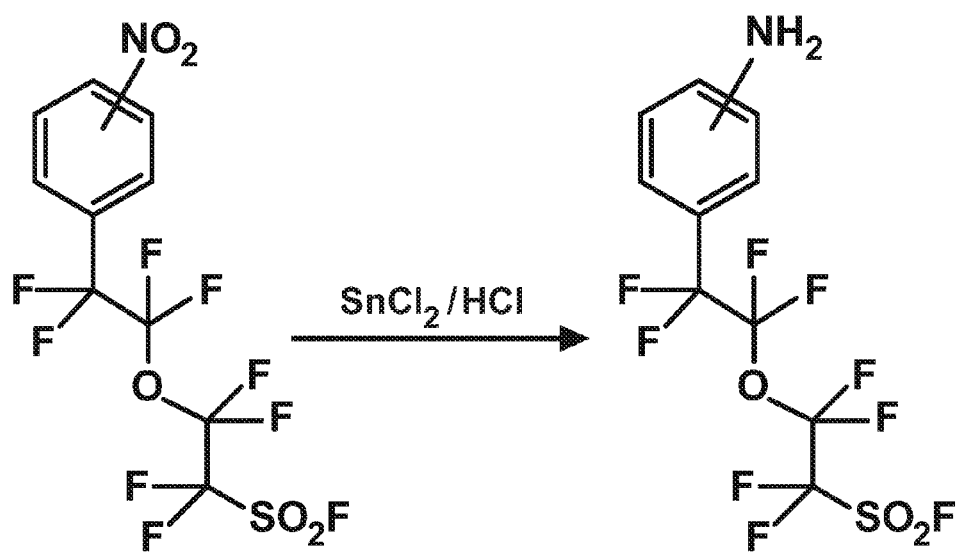
FIG. 6 illustrates a chemical reaction for the formation of $H_2N$—$C_6H_4$—$(CF_2)_2$—O—$(CF_2)_2SO_2F$.

Step 3: Preparation of $H_2N$—$C_6H_4$—$(CF_2)_2$—O—$(CF_2)_2$—$SO_2F$ (see also FIG. 6)

1.036 g (2.46 mmol) of $O_2N$—$C_6H_4$—$(CF_2)_2$—O—$(CF_2)_2$—$SO_2F$, 1.75 g (9.23 mmol) of tin(II) chloride, and 4.5 mL of aqueous 37% HCl was stirred for 26 hrs at 70° C. The reaction mixture was cooled to room temperature. The brown suspension was treated with 20% NaOH until pH 12 was attained, and then the product was extracted with dichloromethane. The organic layer was washed with brine and dried over $MgSO_4$. Evaporation of the solvent yielded 0.8 g of dark brown oil (~83% yield). GC-MS analysis confirmed that the reduction proceeded to >90% conversion, and that the crude product is 85.4% pure. This material can be purified further by column chromatography on silica gel with a mixture of hexanes and methylene chloride (50:50 by volume) as eluent.

Step 4: Carbon Functionalization and Hydrolysis (see also FIG. 7)

0.3 mL of concentrated (16M) $HNO_3$ were added to a suspension of 1 g of Vulcan XC-72 or Pt/Vulcan catalyst in 90 mL of water. Then 1.18 g of $H_2N$—$C_6H_4$—$(CF_2)_2$—O—$(CF_2)_2$—$SO_2F$ (3 mmol) in 10 mL of acetonitrle were added. This mixture was cooled to 0° C. in an ice bath. Next, a solution of 0.227 g (3.3 mmol) of $NaNO_2$ in 5 mL of water was added drop wise, at a rate that kept the reaction temperature under 5° C. The reaction was stirred at 0° C. for two hours. Then 0.5 mL of formic acid were added drop wise, the ice bath removed, and the mixture allowed to warm to room temperature overnight with stirring. Next, the reaction was heated at 70° C. for one hour. The carbon product was isolated by filtration over #50 hardened filter paper and washed with water and acetonitrile. The product was further purified by Soxhlet extraction with acetonitrile.

Step 5: Functional Group Hydrolysis (see also FIG. 8)

The isolated product from step 4 was suspended in a solution of 9 g KOH, 70 mL water, 35 mL DMSO, and 15 mL acetonitrile, which was then heated at 80° C. for one hour. The resulting suspension was centrifuged, and the product rinsed with water until neutral pH was obtained. The product was re-suspended in 10 wt % $HNO_3$ and stirred overnight at room temperature. This suspension was centrifuged, and then the product was rinsed with water until neutral pH was obtained and dried at 80° C.

The attachment of the 5-phenyloctafluoro-3-oxapentane sulfonyl fluoride chains to the Vulcan carbon black particles and the hydrolysis of the sulfonyl fluoride groups to sulfonic acid groups was characterized and confirmed by thermogravimetric analysis of several prepared samples, both before and after hydrolysis. Also, elemental analysis for sulfur and fluorine was conducted on the respective samples, which confirmed a loading of approximately 0.3 mmol/g carbon. Further thermogravimetric analyses under wet and dry flowing inert gas showed that the thermal stability of the functionalized catalyst was improved with respect to the parent species.

A slurry of platinum-bearing Vulcan carbon black particles modified with 5-phenyloctafluoro-3-oxopentane sulfonic acid chains may be prepared in a 5:1 water/isopropanol solution to form an ink. The ink may also contain small bonding particles of membrane composition. The liquid-solids ink mixture may be subjected to ultrasonic vibrations or ball milling for a period of about 30 min to obtain a uniform and well-dispersed mixture for application to a surface of a fuel cell membrane. The ink is dried to form a catalytic electrode layer. The platinum bearing carbon particles are modified with proton conducting fluorocarbon chains attached to the surfaces of the carbon support particles.

Depending on performance specifications for each electrochemical cell of a fuel cell stack the carbon catalyst support materials in all or selected electrodes may be modified to contain fluorocarbon chains with terminal sulfonic acid groups.

In the above illustrated experiments 5-phenyloctafluoro-3-oxapentane sulfonyl fluoride molecular chains were attached to carbon atoms on platinum bearing carbon support particles. The specific composition of these molecular chains was selected to render the proton transport properties of the carbon support particles more compatible with a Nafion® ionomer. But other CFO molecular chains characterized by $-(CF_2)_a-O-(CF_2)_b$ chain segments and/or $-(CF_2)_c-O-(CFX)_d$ chain segments with sulfonyl or sulfonic or other terminal functional groups that form ions in water could have been used as compatible with the perfluorosulfonic acid membranes. For example, and as stated above, CFO molecular chains such as the following may be prepared and attached to a catalyst support:

particle-Ar—$(CF_2)_a$—O—$(CF_2)_b$—X, where

Ar=any aromatic or conjugated moiety, but preferably an aryl ring
a=0 to 500, but preferably an even number between 2 and 50
b=0 to 500, but preferably an even number between 2 and 50, provided at least one of a and b is not equal to 0
X=any moiety with a mobile proton, including but not limited to $SO_3H$, $CO_2H$, $P(O)(OH)_2$, $P(O)(OH)(CF_3)$, $SO_2NHSO_2CF_3$, with the preferred embodiment being $SO_3H$.

And in a more generic alternative embodiment:

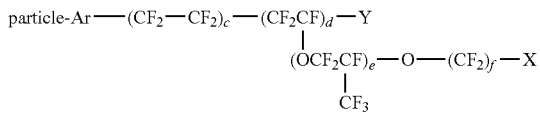

Ar=as above
Y=a terminal group including but not limited to $CF_3$, $CF_2$, OH
c=0 to 20
d=0 to 1000
e=0 to 10
f=0 to 10, provided that at least one of c, d, e, and f is not equal to 0
X=as above Thus, practices of the invention have been illustrated with certain illustrative embodiments which are not intended to limit the scope of the invention.

The invention claimed is:

1. A catalyst material for a catalyzed electrode adjacent to the surface of a proton conducting membrane for an electrochemical cell, the catalyst material comprising electrically conductive carbon support particles carrying smaller catalyst particles, and the carbon support particles having chemically attached fluorinated, linear carbon chains with at least one oxygen atom in each linear chain and with terminal mobile-proton containing groups, the fluorinated chains being connected through an aromatic moiety to the surfaces of the support particles, the fluorinated carbon chains connected to the support particles being characterized by the formula:

particle-Ar—$(CF_2)_a$—O—$(CF_2)_b$—X, where

Ar=an aryl ring, a=an even number from 2 to 50, b=an even number form 2 to 50, and X=any one or more of $SO_3H$, $CO_2H$, $P(O)(OH)_2$, $P(O)(OH)(CF_3)$, and $SO_2NHSO_2CF_3$.

2. A catalyst material as recited in claim 1 in which the proton conducting membrane comprises carbon chains with terminal mobile-proton groups.

3. A catalyst material as recited in claim 1 in which the polymer membrane is a perfluorosulfonic acid membrane.

4. A catalyst material as recited in claim 1 in which the fluorinated carbon chains are characterized by the formula:

—Ar—$(CF_2)_2$—O—$(CF_2)_2$—$SO_3H$, where Ar is a phenyl radical.

5. An electrochemical cell comprising a polymer electrolyte membrane with a catalyzed electrode layer on a surface of the electrolyte membrane, the membrane polymer comprising pendant fluorinated carbon chains with terminal mobile-proton containing groups for proton conductivity through the membrane, the catalyst electrode layer comprising particles of carbon carrying smaller catalyst particles, and the carbon particles having fluorinated, linear carbon chains with at least one oxygen atom in each linear chain and with terminal mobile proton-containing groups, the fluorinated chains being connected through aromatic moieties to carbon atoms at the surface of the carbon particles, the fluorinated carbon chains connected to the carbon particles being characterized by the formula:

particle-Ar—$(CF_2)_a$—O—$(CF_2)_b$—X, where

Ar=an aryl ring, a=an even number from 2 to 50, b=an even number form 2 to 50, and X=any one or more of $SO_3H$, $CO_2H$, $P(O)(OH)_2$, $P(O)(OH)(CF_3)$, and $SO_2NHSO_2CF_3$.

6. An electrochemical cell as recited in claim 5 in which the polymer membrane is a perfluorosulfonic acid membrane.

7. An electrochemical cell as recited in claim 5 in which the carbon chains connected to the carbon particles are characterized by the formula:

—Ar—$(CF_2)_2$—O—$(CF_2)_2$—$SO_3H$, where Ar is a phenyl radical.

* * * * *